United States Patent [19]

Merger et al.

[11] Patent Number: 4,482,499

[45] Date of Patent: Nov. 13, 1984

[54] PROCESS FOR THE PREPARATION OF ISOCYANATES BY THERMAL CLEAVING OF URETHANES

[75] Inventors: Franz Merger, Frankenthal; Gerhard Nestler, Ludwigshafen; Rolf Platz, Mannheim; Friedrich Towae, Ludwigshafen; Hans Hellbach, Lampertheim, all of Fed. Rep. of Germany

[73] Assignee: BASF Aktiengesellschaft, Ludwigshafen, Fed. Rep. of Germany

[21] Appl. No.: 436,283

[22] Filed: Oct. 25, 1982

[30] Foreign Application Priority Data

Oct. 28, 1981 [DE] Fed. Rep. of Germany ....... 3142627

[51] Int. Cl.³ ........................................... C07C 118/00
[52] U.S. Cl. ................................................. 260/453 P
[58] Field of Search ..................................... 260/453 P

[56] References Cited

U.S. PATENT DOCUMENTS 2,409,712  10/1946  Schweitzer et al. ............ 260/453 P
3,870,739  3/1975   DeLaMater et al. ............... 260/453
4,081,472  3/1978   Tsumura et al. .................... 260/453

*Primary Examiner*—Dolph H. Torrence
*Attorney, Agent, or Firm*—William G. Conger; Joseph D. Michaels; David L. Hedden

[57] ABSTRACT

Organic isocyanates, preferably alkyl, mono-, di- and/or polyisocyanates or aryl-mono-, di- and/or polyisocyanates, are prepared by thermally cleaving the corresponding urethanes at temperatures of 175° C. to 600° C. in the presence of carbon, preferably in an agitated carbon bed or in a fluidized bed containing carbon.

11 Claims, No Drawings

PROCESS FOR THE PREPARATION OF ISOCYANATES BY THERMAL CLEAVING OF URETHANES

BACKGROUND OF THE INVENTION

1. Field of the Invention

This invention relates to the preparation of organic isocyanates. The organic isocyanates are prepared by thermally cleaving urethanes at temperatures of 175° C. to 600° C. in the presence of carbon.

2. Description of the Prior Art

It is known tha N-substituted urethanes can be thermally cleaved into isocyanates in the gas phase or in the liquid phase. The thermal cleaving is frequently accompanied by various undesirable secondary reactions. Examples of such reactions include the decarboxylation reaction of urethanes which may be accompanied by the formation of primary and secondary amines as well as of olefins. Reactions between the formed isocyanate and urethane result in allophanates and reactions with an amine result in ureas; moreover, polymerization of the isocyanates results in isocyanurates.

According to data in German published application No. 19 44 719 (British Pat. No. 1,247,451), the pyrolysis of urethanes in the vapor phase is carried out at temperatures of 400° C. to 600° C. in the presence of Lewis acids as catalysts with the isocyanate and the alcohol being separated by fractional condensation. Toluene diisocyanate is produced, for example, by pyrolysis of toluene-2,4-diethylurethane in the presence of iron (III)-chloride. Drawbacks of the reaction include low yields combined with considerable amounts of a polymeric by-product, decomposition of the catalyst, and corrosion of the reaction equipment. German published application No. 24 10 505 (U.S. Pat. No. 3,870,739) describes a process wherein the urethane is cleaved at a temperature of 350° C. to 550° C. at a pressure of less than (m+1) times that of the isocyanate vapor pressure in a catalyst-free pyrolysis zone within 15 seconds. One of the drawbacks of this method is that a large amount of heat required for the endothermal cleaving must be made available to the powdered urethane within a very short period of time. Moreover, a solid polymer is incurred as a by-product and the separation of this by-product renders the implementation of a continuous process more difficult.

The thermal cleaving of urethanes in the liquid phase is described, for example, in German application No. 24 21 503 (U.S. Pat. No. 3,962,302) and German application No. 25 30 001 (U.S. Pat. No. 3,919,280). According to data in German application No. 24 21 503, the urethanes are dissolved in an inert solvent such as alkylbenzenes, linear and cyclic hydrocarbons and/or phthalates and are cleaved at temperatures of 175° C. to 350° C. under normal or increased pressure. The resultant isocyanate and alcohol are isolated and separated with the aid of the solvent as a carrier and/or by using an inert gas as carrier. According to German Application No. 25 30 001, higher molecular optionally substituted aliphatic, cycloaliphatic or aromatic hydrocarbons, ethers, esters or keltones are used as reaction media. Distillation is utilized for separating the cleaving products with isocyanate alcohol and carrier material being removed by distillation overhead whereas the reaction medium remains as bottom fraction.

For the preparation of aromatic isocyanates, the urethanes, according to German published application No. 26 35 490 (U.S. Pat. No. 4,081, 472) , are brought in contact with a solution of at least one metal ion such as ions of copper, zinc, aluminum, tin, titanium, vanadium, iron, cobalt and nickel as catalyst, dissolved in a solvent having a boiling point of 200° C. in a metal concentration of at least 0.001 percent by weight based on the solvent at temperatures of 150° C. to 300° C. under reduced pressure. The resultant cleaved products are separated by fractional condensation. However, this results in small amounts of non-distillable polymerization products formed during the reaction remaining in the solvent residue containing the catalyst. After a certain amount of time, this necessitates additional cleaning operations of the solvents containing the catalytic metal ions.

According to German Published Application No.29 42 543, very good cleaving results are obtained if the urethanes are cleaved on catalytically effective, high surface metals which are present in the heterogeneous phase. The drawback of this process is that the metals used as catalysts lose their catalytic activity in time as a result of being coated, thereby, also necessitating additional cleaning operations.

SUMMARY OF THE INVENTION

The subject invention relates to a process for the preparation of isocyanates which comprises thermally cleaving urethanes at temperatures of 175° C. to 600° C. in the presence of carbon. It has been found that urethanes can be thermally cleaved in a very simple manner with good yields and a high degree of purity in an economically advantageous manner.

The monoisocyanates obtained in accordance with this invention are valuable intermediates for the preparation of pesticides, dyestuffs, and auxiliaries. The diisocyanates and polyisocyanates are preferably used for the preparation of polyurethane plastics.

DESCRIPTION OF THE PREFERRED EMBODIMENT

The carbon to be used in accordance with this invention not only is a good heat transfer agent but also an inexpensive material which does not require regeneration after prolonged usage when it is deactivated or has become lumpy, for example, as a result of the polymeric by- or decomposition products. On the other hand, it can be destroyed by incineration without residues and in an environmentally sound manner.

The carbon to be used in accordance with this invention has a bulk density of 700 grams to 1000 grams per liter, preferably of 750 grams to 950 grams per liter. It may be used in the form of powder or pressed cakes. Powdered carbon has an average grain size of 0.01 mm to 10 mm, preferably of 0.1 mm to 2 mm. The pressed coal may be present, for example, in the form of spheres, rings, cylinders or pellets. Using spherical pressed carbon cakes, the spheres generally have diameters of 0.2 mm to 10 mm, preferably 0.5 mm to 5 mm. In the case of cylindrical shaped pressed cakes, cylinders having a length of 2 mm to 15 mm and a diameter of 2 mm to 6 mm are generally used. Non-spherical or cylindrical shaped pressed cakes generally have a volume which corresponds with that of the cylinder shaped pressed bodies.

The powdered or pressed carbon may be poured into a reaction vessel, for example, a tube or tunnel furnace in the form of a fixed bed. The chosen dimension of the fixed carbon bed is preferably determined by the feasibility of applying the heat needed for the cleaving to take place.

The reaction vessel generally have a columnar form and may have any desired cross section, for example, that of a square or an elipse. Preferably used are long, cylindrical reaction vessels. The ratio of internal diameter to length of the reaction vessel generally is 1:2 to 1:100, preferably 1:10 to 1:40. The reaction vessels may be aligned vertically or horizontally and may also have intermediate layers. Preferably used are vertical tube furnaces where the tube diameter is approximately 10 mm to 100 mm. However, cleaving of the urethanes according to the process of this invention is preferably carried out in an agitated carbon bed or in a fluidized bed with carbon filling.

A suitable reaction vessel, for example, is a carbon filled vessel equipped with a helical ribbon impeller or an anchor agitator. Advantageously, the vessels are selected with a ratio of height to diameter of 0.5 to 2.5:1, preferably of 0.7 to 2:1 and a ratio of the height of the agitator in the vessel (measured as vertical distance from the inlet opening of the agitator to the level of the agitator tip) to the height of the carbon bed of 0.8 to 1:1.

To implement the process of this invention, all other commonly used fluidized bed installations are suited which contain carbon as the solid material. Preferably used, however, are fluidized beds which primarily consist of a preferably cylindrical fluidizing vessel, the internal diameter of which is in a relationship to the length of generally 1:0.5 to 1:7, preferably 1:1 to 1:3 containing the fluidized bed. The fluidized bed may contain a baffle plate for the fluidizing gas which may, for example, consist of a frit plate, a perforated tray or a bubble-plate tray or a Conidur precision drilled plate; a nozzle for product feed and the product and off-gas discharges which may optionally be facilitated via a filter located in the fluidizing vessel or via cyclones; an mechanical size reduction device for the carbon with an optionally preceding classifier, for example, a mill or a rotating hammer pulverizer which may be installed inside or outside of the fluidizing vessel and which may counteract a possibly occuring grain enlargement and produces new granulating nuclei; and heating installations.

It was particularly surprising that the urethanes which are injected in the fluidized bed either in vapor form, dissolved or in molten form do not plug the openings in the baffle tray at the fluidized bed reactor or cake together with the cleavage product resulting in large agglomerates which are no longer fluidizable under economic conditions. In spite of the wide distribution of residence times in the fluidized bed, the resultant isocyanates essentially suffer no thermal damage.

Another advantage is the fact that the fluidized bed device does not have any mechanically moved parts. This results in low susceptibility to repairs, low maintenance and investment costs, and high space-time yields. Since the cleavage products are generally separated under normal pressure, sealing problems are not incurred. The required heat can be simply introduced via the fluidizing gas and can be transferred to the fluidized bed or can be transferred via fixtures installed in the fluidized bed.

Finally, an additional advantage of the process according to this invention is the fact that the consumed carbon residue is obtained in a low dust form which is easily handled and pourable.

In accordance with the process of this invention, the carbon bed for thermal cleaving of the urethanes is charged with 20 to 1000, preferably 50 to 500 urethane equivalents per liter of carbon an hour.

The thermal cleaving can be carried out at temperatures from 175° C. to 600° C., preferably at 220° C. to 450° C. on a batch-type or continuous basis under reduced, normal or increased pressure, for example, under pressures of 0.01 bar to 5 bars, preferably 0.1 bar to 1.0 bar.

As already mentioned, the urethanes may be introduced into the carbon bed either as a vapor, in liquid or solid form, for example, as a powder, as a suspension or, preferably, as a solution in a solvent which is inert under the reaction conditions.

Cleaving of the urethanes and separation of the cleaved products by distillation of the alcohol, the isocyanate and, optionally, the solvent may take place simultaneously or in sequence. In order to achieve a long service life of the carbon bed and optimum isocyanate yields, the cleaved products are stripped from the carbon bed as quantitatively as possible by using a stripping agent. Suitable stripping agents include solvents. Stripping agents with boiling points between the boiling points of the resultant isocyanate and the alcohol are used on a preferred basis.

The urethanes are advantageously introduced in the carbon bed in a solvent which is simultaneously a suitable stripping agent with urethane concentrations in the solvent of 1 to 70 percent by weight, preferably 5 to 50 percent by weight being advantageous. However, it is also possible to separately introduce the stripping agent into the carbon bed. If a solvent is not used for cleaving, an additional stripping agent must be introduced into the carbon bed with the weight ratio of urethane to stripping agent being 1:0.5 to 20, preferably 1:1 to 10. It is also possible to direct an inert gas such as carbon monoxide or preferably nitrogen through the carbon bed in addition to the stripping agent unless an inert gas is used for fluidizing the carbon bed. In a preferred version, the resultant cleaved products and the solvent and/or stripping agent are directed into one or several separating columns with the alcohol and isocyanate being separated optionally with the use of the stripping agent which boils between the alcohol and isocyanate. It is also possible to condense the cleaved products, solvent and stripping agent by fractionalization.

Examples of solvents or stripping agents include aliphatic hydrocarbons such as the higher alkanes, decane, undecane, dodecane, tridecane, tetradecane, pentadecane, hexadecane, heptadecane, decalin TM, liquid paraffin, oil fractions of paraffins which are normally used as lubricating oils, cooling oils or cutting oils; alicyclic hydrocarbons such as crude oil fractions of the naphthene series; optionally substituted aromatic hydrocarbons such as naphthalene, 1-and 2-methylnaphthalene, 1,2-, 1,4-,1,6-, 2,7-, 2,6-and 2,3-dimethylnaphthalene, 1-ethylnaphthalene, phenylnaphthalene, benzylnaphthalene, toluene, 1,2-,1,3- and 1,4-dimethylbenzene, 1,2,4-and 1,3,5-trimethylbenzene, 1,2,3,5- and 1 2,4,5-tetramethylbenzene, 1,3,5triethylbenzene, hexylbenzene, heltylbenzene, hexaethylbenzene, diphenyl, 4,4'-dimethyldiphenyl, dibenzyl, diphenylmethane and 4,4'-dimethyldiphenylmethane; halogen substituted aromatic hydrocarbons such as chlorobenzene, 1,2- and 1,4- dichlorobenzene, 1,4-diodobenzene, 1,2,3- and1,3,5-trichlorobenzene, 1,2,3,4-, 1,2,3,4- and 1,2,4,5-tetrahlorobenzene, pentachlorobenzene, 1- and 2-fluoronaphthalene, 1- and 2-chloronaphthalene, 1- and 2-iodonaphthalene and diphenyldichloromethane; nitro group-containing aromatic hydrocarbons such as nitrobenzene, 3-nitrotoluene, 2-nitro- m-xylene, 5-nitro-m-xylene and 4-nitroanisol; aliphatic and aromatic ketones such as cyclohexanone, cycloheptanone, di-n-butylketone, di-n-amylketone, α-tetralon, acetophenone, propiophenone, benzophenone, 3methylbenzophenone, dodecanone-2 and tridecanone- 2; sulfones and carboxylates such as sulfolane, diethylsulfone, phthalic acid dimethyl ester, phthalic acid diethyl ester, benzoic acid propyl ester, lauric acid ethyl ester; and ethers such as diethylene glycol dimethyl ether, diethylene glycol diethyl ether, diisoamyl ether, di-n-amyl ether, resorcin dimethyl ether, resorcin diethyl ether, phenyl octyl ether, phenyl benzyl ether, dibenzyl ether, diphenyl ether, α-methylnaphthyl ether and β-ethyl naphthyl ether.

Optionally substituted aromatic hydrocarbons such as benzene, toluene, 1,2-, 1,3- and 1,4-dimethylbenzene, 1,2,4- and 1,3,5-trimethylbenzene, 1,2,3,5- and 1,2,4,5-tetramethylbenzene, 1,3,5-triethylbenzene, hexybenzene, heptylbenzene, octylbenzene, nonylbenzene, decylbenzene; halogen substituted aromatic hydrocarbons such as nitro benzene, 3-nitrotoluene, 2-nitro-m-xylene, 5-nitro-m-xylene and 4-nitroanisol; aliphatic and aromatic ketones such as cyclohexanone, cycloheptanone, di-n-butylketone, di-n-amyl- ketone; and ethers such as diethylene glycol-dimethylether, diethylene glycol diethylether, diisoamylether, di-n-amylethers have proven to work particularly well and are, therefore, used on a preferred basis.

Urethanes which are cleaved thermally into isocyanate and alcohol in accordance with the process of this invention have a general formula

in which the following symbols are used:
R represents a heterocyclic radical or preferably an optionally substituted aryl- and/or alkyl-radical wherein the alkyl radical can be linear, branched or cyclic and, optionally, also hetero atoms such as sulfur, oxygen or nitrogen and in which the aryl radical may contain methylene groups in bonded form as bridge members,
R' represents an optionally aryl- and/or alkyl radical with 1 to 20 carbon atoms, prerferably 1 to 10 carbon atoms, or a cycloaliphatic radical with 3 to 15 carbon atoms, preferably 3 to 7 carbon atoms, and
n represents a whole number of 1 to 4 and higher, preferably 1 to 3 and particularly 2.

Examples for radicals R in the case of optionally substituted aryl urethanes include the radicals of aromatic monoamines such as aniline, substituted anilines such as anilines substituted in the 2-, 3- and/or 4-position by a nitro group, methyl group, ethyl group, n-propyl group, isopropyl group, n-butyl group, isobutyl group, secondary butyl group, tertiary butyl group or a chlorine atom ortho-, meta- and/or para- hydroxy-, methoxy-, ethoxy-, propoxy-, isopropoxy-, N-butoxy-, isobutoxy-, secondary butoxy- and tertiary butoxyaniline; benzoic acid alkyl esters with 1 to 4 carbon atoms in the alkyl radical substituted by an amino group in the n- and/or p-position; n-alkoxycarbonylamino benzenes and toluenes with 1 to 4 carbon atoms in the alkyl radical substituted by an amino group in the m- and p- position; α- and β-naphthylamine; aromatic diamines such as 1,3- and 1,4-diaminobenzene; 1,3-diaminobenzene substituted in the 2- and/or 4-position by a nitro group, a methyl-, ethyl-, n-propyl-, isopropyl-, n-butyl-, isobutyl-, secondary-butyl-, tertiary-butyl-, methoxy-, ethoxy-, n-propoxy-, isopropoxy-, n-butoxy-, isobutoxy-, secondary-butoxy-, tertiary-butoxy group or a halogen atom, preferably a fluorine or a chlorine atom, or 1,4-diamino benzene, 1,5- and 1,8-diaminonaphthalene, 4,4'-diaminophenyl, 2,2'-, 2,4'- and 4,4'-diaminodiphenylmethane substituted in the 2-position or the corresponding isomer mixtures and aromatic polyamines such as 1,3,5-triaminobenzene, 2,4,6-triamino- toluene and 1,3,5-triaminonaphthalene.

In the case of optionally substituted alkyl urethanes, examples for the radical R include the radicals of aliphatic monoamines such as methylamine, ethylamine, propylamine, isopropylamine, n-butylamine, secondary butylamine, tertiary butylamine, isobutylamine, 2- and 3-methylbutylamine, neopentylamine, n-pentylamine, 2-methyl-pentylamine, secondary-iso-amylamine, n-hexylamine, 2-methylhexylamine, 2-ethylhexylamine, n-heptylamine, n-octylamine, n-nonylamine, n-decylamine, n-dodecylamine, 2-phenylpropylamine, benzylamine, cyclopentylamine, cyclo-hexylamine, tertiary butylcyclohexylamine; aliphatic diamines such as ethylenediamine, 1,3- and 1,2-propylenediamine, 2,2-dimethyl-1,3-propylenediamine, 1,4-butylenediamine, 1,5-pentamethylenediamine, 1,6-hexamethylenediamine, 2,2,4-trimethyl-1,6-hexamethylenediamine, 1,8-octaethylenediamine, 1,10-decylenediamine, 1,12-dodecylenediamine and 1,4hexahydroxylylenediamine; cycloaliphatic diamines such as 1,2-, 1,3- and 1,4-cyclohexanediamine, 2,4- and 2,6-hexahydrotoluenediamine as well as the corresponding isomer mixtures; aliphatic-cycloaliphatic diamines such as 4,4'-, 2,4'- and 2,2'-diaminodicyclohexylmethane as well as the corresponding isomer mixture, 2,2-bis(4-aminocyclohexyl)-propane, 3-aminomethyl-3,5,5-trimethylcyclohexylamine; and dicyclopentadienyl compounds having the formula

which contain in bonded form hetero atoms or heterocyclic radicals such as 3,3'-diamino-dipropylether, optionally, substituted N,N'-bis(aminoalkyl)piperazine, such as N,N'-bis(2,2-dimethyl-3-aminopropyl)piperazine and N,N'-bis-(aminopropyl)piperazine.

Typical examples for aryl urethanes which are thermally cleavable according to the process of this invention, include: N-phenyl-methyl urethane, N-phenylethyl urethane, 3,5-dichlorophenyl ethyl urethane, 4-methylphenyl ethyl urethane, 2,4- and 2,6-toluene dimethyl urethane as well as the corresponding isomer mixtures, 2,4- and 2,6-toluene dietyl urethane, 2,4- and 2,6-toluene dibutyl urethane, 1,5-napthylene diethyl urethane, 4,4'-, 2,4'-, 2,2'-diphenylmethane dimethyl urethane, 4,4'-, 2,4'- and 2,2'-diphenylmethane diethyl urethane, 4,4'-, 2,4'- and 2,2'-diphenylmethane dibutyl urethane, 4,4'-, 2,4'-, and 2,2'-diphenylmethane dihexyl urethane, as well as the corresponding isomer mixtures.

Typical examples for alkyl urethanes include: N-methyl octyl urethane, N-methyl hexyl urethane, N- ethyl dodecyl urethane, N-methyl-phenyl urethane, N-ethyl phenyl urethane, N-propyl phenyl urethane, N-propyl decyl urethane, N-cyclohexyl methyl urethane, 1,6-hexamethylene dibutyl urethane, 1,6-hexamethylene diethyl urethane, 1,6-hexamethylene dimethyl urethane, 2,2,4-trimethyl-1,6-hexamethylene dibutyl urethane, 1,4-hexahydroxylylene diethyl urethane, 1,4-cyclohexyl dimethyl urethane, 1,4-cyclohexyl dibutyl urethane and 3-(butoxycarbonyl aminomethyl)-3,5,5-trimethyl cyclohexy butyl urethane.

The parts referred to in the Examples are parts by weight. Parts by weight relative to volume parts are like kilograms relative to liters.

EXAMPLE 1

As cleaving equipment, an agitator vessel with 500 volume parts was used in which 290 parts of carbon beads having a particle size of 0.5 mm to 1.0 mm were intensively agitated and heated to 370° C. to 375° C. The apparatus discharges through a double jacketed tube heated to 310° C. to 320° C., into a separating column filled with wire rings having a diameter of 3 mm. The column was equipped with seven separating stages having a concentrating and a discharge section in which o-xylene boiled under total reflux.

Within a period of one hour, a solution of 40 parts of 2,4-toluene diethyl urethane in 160 parts of o-xylene was introduced into the agitated carbon bed and in addition to this, 100 liters of nitrogen per liter of reaction mixture an hour were blown through the equipment. As soon as the temperature at the head of the separating column had reached the boiling temperature of the alcohol, takeoff of the product was begun. After complete reaction, the isocyanate concentrate in the flask and the xylene/alcohol mixture taken from the head of the column were analyzed by means of gas chromatograph using the method of the "Internal Standard." It was found that 22.7 parts of 2,4-toluene diisocyanate (88.5 percent of theory) and 13.3 parts of ethanol (98.1 percent of theory) were formed. Ninety-eight percent of 2,4-toluene diethyl urethane were converted (determined by high pressure liquid chromatography).

EXAMPLES 2-8

The procedure was analogous with that explained in Example 1 except other urethane and solvents and/or stripping agents were used. The results are listed in Table I.

TABLE I

| Example No. | Urethane | Solvent and/or Stripping Agent | Conversion % | Isocyanate | Yield % |
| --- | --- | --- | --- | --- | --- |
| 2 | N—phenyl methyl urethane | Toluene | 76.3 | Phenyl isocyanate | 99.1 |
| 3 | 2,4-bis(butoxycarbonylamino)-toluene | o-xylene | 94.1 | 2,4-toluene-diisocyante | 92.2 |
| 4 | N—(3,5-dichlorophenyl)-methyl urethane | Ethylene glycol dimethyl ether | 89.3 | 3,5-dichlorophenyl-isocyanate | 96.4 |
| 5 | Hexamethylene-1,6-diethyl-urethane | Toluene | 67.2 | Hexamethylene diisocyanate | 71.5 |
| 6 | Hexamethylene-1,6-dibutyl-urethane | o-xylene | 81.0 | Hexamethylene diisocyanate | 89.8 |
| 7 | N—propylphenyl urethane | Toluene | 76.7 | Propyl isocyanate | 98.7 |
| 8 | 1-(butoxycarbonyl amino)-3-(butoxycarbonyl amino methyl)-3,5,5-trimethylcyclohexane | o-xylene | 58.8 | Isophorone diisocyanate | 71.6 |

EXAMPLE 9

In a cylindrical fluidizing vessel with a diameter of 6 cam and a height of 30 cm heated externally and electrically to an inside temperature of 350° C. and equipped with a frit as fluidizing baffle and a nozzle installed on the side 5 cm above the baffle, 200 grams of carbon dust with an average grain diameter of 0.1 to 0.5 mm were introduced. The fluidizing gas, nitrogen, which was preheated in a heat exchanger was introduced via the baffle. During a period of one hour, a solution of 10 percent by weight of toluene-2,4-dibutyl urethane in xylene was injected and, after dust removal with the aid of a wire mesh filter, the mixture of resultant toluene-2,4-diisocyanate, butanol, xylene and carbamate group-containing monoisocyanate were condensed and fractioned into four vessels. The fractions were analyzed gas chromatographically according to the "Internal Standard" method. The analysis showed that 19.1 parts of toluene-2,4-dissocyanate (88.4 percent of theory), 16.4 parts butanol (89.4 percent of theory) as well as carbamate containing monoisocyanate were formed.

EXAMPLE 10-12

The procedure was similar to that of Example 9 but different urethanes, solvents and stripping agents and cleaving temperatures were used. The results are listed in Table II.

TABLE II

| Example No. | Urethanes | Solvent | Cleaving Temperature °C. | Isocyanates | Yield % |
| --- | --- | --- | --- | --- | --- |
| 10 | Toluene-2,4-diethyl urethane | Toluene | 370 | 2,4-toluene diisocyanate | 91.7 |
| 11 | N—phenyl-methyl urethane | Toluene | 320 | Phenyl isocyanate | 98.7 |
| 12 | Hexamethylene-1,6-dibutyl urethane | Ethylene glycol dimethyl ether | 380 | 1,6-hexamethylene diisocyanate | 83.8 |

The embodiments of the invention in which an exclusive privilege or property is claimed are defined as follows:

1. A process for the preparation of an organic isocyanate which comprises thermally cleaving a urethane at temperatures of 175° C. to 600° C. in the presence of carbon.

2. The process of claim 1 wherein the carbon is present in the form of a powder having an average grain size of 0.01 to 10 mm.

3. The process of claim 1 wherein the cleaving takes place in an agitated carbon bed.

4. The process of claim 1 wherein the carbon is present as the solid material in a fluidized bed.

5. The process of claim 1 wherein the cleaving takes place in a fluidized bed.

6. The process of claim 1 wherein the cleavage products, the isocyanate and alcohol, are separated from the reaction mixture by way of a stripping agent.

7. The process of claim 6 wherein the stripping agent has a boiling point which is located between the boiling points of the isocyanate and the alcohol obtained by the cleaving process.

8. The process of claim 6 wherein a solvent which is inert under the reaction conditions is used as the stripping agent.

9. The process of claim 6 wherein an inert gas is used in addition to the stripping agent in order to separate the cleavage products.

10. The process of claim 1 wherein the urethane cleaved is selected from the group consisting of an alkyl-, mono-, di-, and polyurethane, and mixtures thereof.

11. The process of claim 1 wherein the urethane cleaved is selected from the group consisting of an aryl-, mono-, di-, and polyurethane, and mixtures thereof.

* * * * *